US010518259B2

(12) United States Patent
Wright

(10) Patent No.: US 10,518,259 B2
(45) Date of Patent: Dec. 31, 2019

(54) DISPOSABLE DIAGNOSTIC DEVICE WITH VOLUMETRIC CONTROL OF SAMPLE AND REAGENTS AND METHOD OF PERFORMING A DIAGNOSIS THEREWITH

(71) Applicant: David W. Wright, Littleton, CO (US)

(72) Inventor: David W. Wright, Littleton, CO (US)

( * ) Notice: Subject to any disclaimer, the term of this patent is extended or adjusted under 35 U.S.C. 154(b) by 106 days.

(21) Appl. No.: 15/648,171

(22) Filed: Jul. 12, 2017

(65) Prior Publication Data

US 2018/0015453 A1 Jan. 18, 2018

Related U.S. Application Data

(60) Provisional application No. 62/361,121, filed on Jul. 12, 2016.

(51) Int. Cl.
*B01L 3/00* (2006.01)
*G01N 15/06* (2006.01)
(Continued)

(52) U.S. Cl.
CPC ......... *B01L 3/502* (2013.01); *B01L 3/502715* (2013.01); *B01L 3/502738* (2013.01); *B01L 2200/026* (2013.01); *B01L 2200/0605* (2013.01); *B01L 2200/0621* (2013.01); *B01L 2200/0684* (2013.01); *B01L 2200/0689* (2013.01); *B01L 2200/16* (2013.01); *B01L 2300/0627* (2013.01); *B01L 2300/0672* (2013.01); *B01L 2300/0816* (2013.01); *B01L 2300/0838* (2013.01); *B01L 2300/0877* (2013.01); *B01L 2300/0883* (2013.01); *B01L 2300/0887* (2013.01);
(Continued)

(58) Field of Classification Search
CPC .......... B01L 3/00; G01N 15/06; G01N 33/00; G01N 33/48; G01N 1/00; G01N 1/10; G01N 35/00; A61J 1/06
USPC ...... 422/68.1, 502, 503, 504, 537, 547, 554; 436/43, 63, 64, 65, 66, 174, 180
See application file for complete search history.

(56) References Cited

U.S. PATENT DOCUMENTS

2012/0045826 A1* 2/2012 Yantz ................ A61B 5/15186 435/288.7
2013/0331298 A1* 12/2013 Rea ...................... C12Q 1/6844 506/16

(Continued)

*Primary Examiner* — Brian J. Sines
(74) *Attorney, Agent, or Firm* — John D. Wright; Dickinson Wright PLLC

(57) ABSTRACT

A single-use, consumable diagnostic cartridge and method of performing a diagnostic test are provided. The cartridge has a sample inlet opening, an inlet port, a sample receiving chamber, an analysis chamber and a fluid channel extending between the sample receiving chamber and analysis chamber. A rupturable blister contains a fluid for selective mixing with a sample selectively disposed in the sample receiving chamber. A valve member, having a sample through port and a fluid passage, is selectively moveable between closed and open states. In the closed state, the fluid passage is out of fluid communication with the sample, and the sample through port is registered with the sample inlet opening and the sample receiving chamber. In the open state, the fluid passage extends between the inlet port and the sample receiving chamber to allow fluid dispelled from the blister to transport the sample to the analysis chamber.

11 Claims, 6 Drawing Sheets

(51) Int. Cl.
*G01N 33/00* (2006.01)
*A61J 1/06* (2006.01)

(52) U.S. Cl.
CPC . *B01L 2400/0481* (2013.01); *B01L 2400/065* (2013.01); *B01L 2400/0633* (2013.01); *B01L 2400/0683* (2013.01)

(56) References Cited

U.S. PATENT DOCUMENTS

| | | | | |
|---|---|---|---|---|
| 2016/0129437 | A1* | 5/2016 | Kayyem | B01L 3/502<br>204/600 |
| 2016/0129445 | A1* | 5/2016 | Corey | B01L 7/52<br>435/286.1 |
| 2016/0130640 | A1* | 5/2016 | Wright | B01F 7/00116<br>506/39 |
| 2016/0220994 | A1* | 8/2016 | Wright | A61B 5/150022 |
| 2016/0346778 | A1* | 12/2016 | Wright | B01L 3/502 |
| 2017/0259268 | A1* | 9/2017 | Wright | B01L 3/50273 |

* cited by examiner

FIG. 4
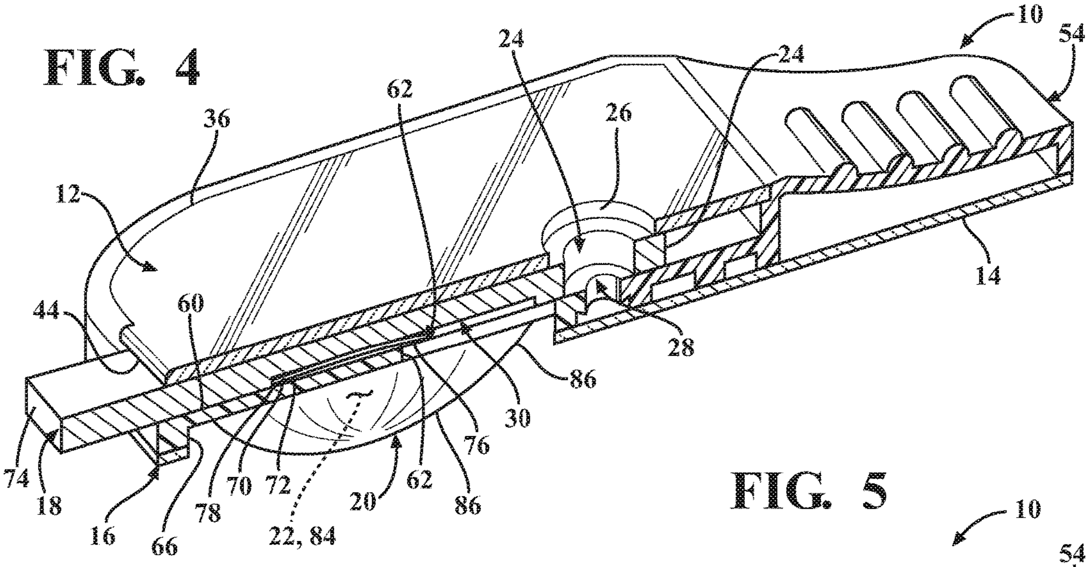
FIG. 5
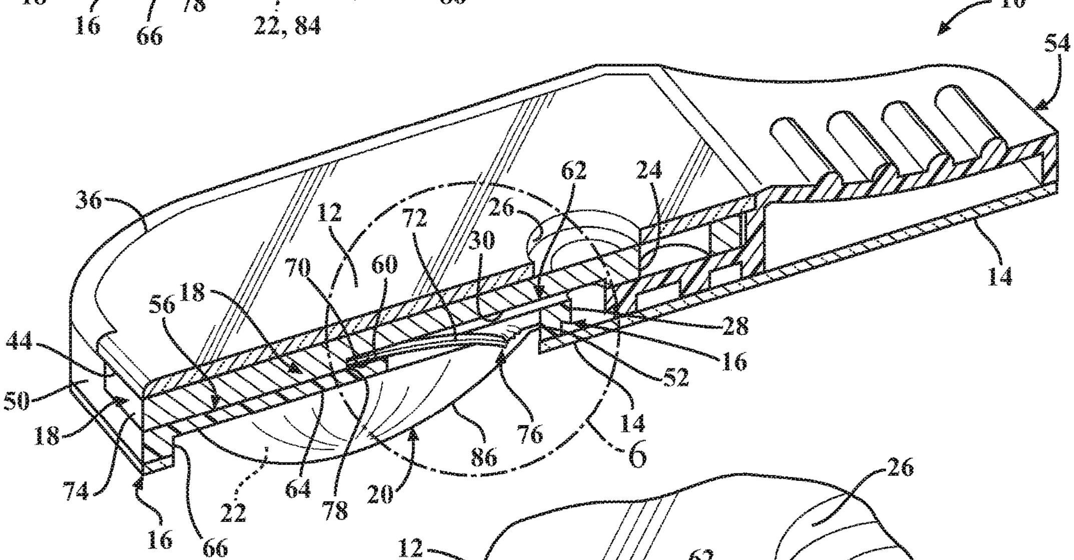
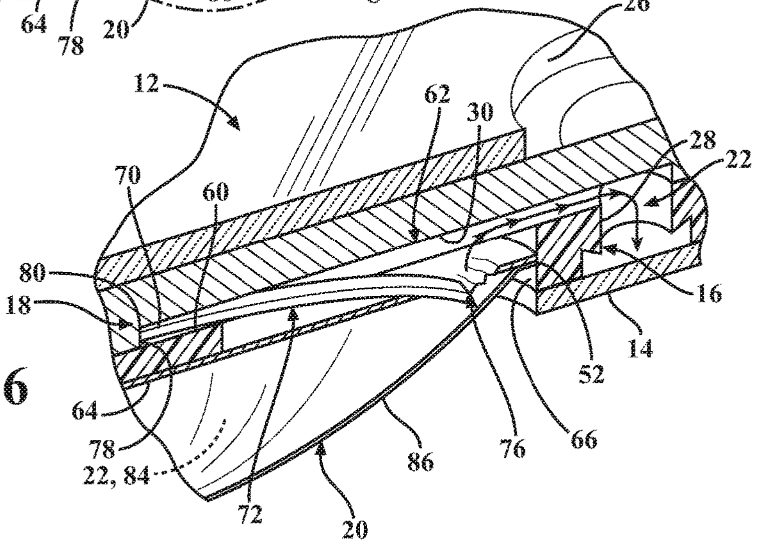
FIG. 6

DISPOSABLE DIAGNOSTIC DEVICE WITH VOLUMETRIC CONTROL OF SAMPLE AND REAGENTS AND METHOD OF PERFORMING A DIAGNOSIS THEREWITH

CROSS-REFERENCE TO RELATED APPLICATION

This application claims the benefit of U.S. Provisional Application Ser. No. 62/361,121, filed Jul. 12, 2016, which is incorporated herein by way of reference in its entirety.

BACKGROUND

1. Technical Field

This invention relates generally to in-vitro diagnostics, and more particularly to disposable diagnostic cartridges and apparatus and methods for controlling volume of the sample and reagents to be assayed.

2. Related Art

Diagnostic tests are increasingly being used to determine the state or condition of a biological environment, such as in human healthcare, agriculture, livestock management, municipal systems management, and national defense, by way of example and without limitation. A new market is emerging wherein diagnostic tests are being performed at the point-of-care. The diagnostic test can be complex, requiring multiple fluids and multiple steps to execute an assay. An assay is a sequence of steps or procedures used to measure the presence or absence of a substance in a sample, the amount of a substance in a sample, or the characteristics of a sample. An example of a common and relatively simple point-of-care assay, which can be readily conducted by a layperson, is a blood glucose test. In this test, generally speaking, the blood is mixed with glucose oxidase, which reacts with the glucose in the sample, creating gluconic acid, wherein the gluconic acid reacts with a chemical, typically ferricyanide, producing ferrocyanide. Current is passed through the ferrocyanide and the impedance reflects the amount of glucose present.

Although the aforementioned blood glucose assay is relatively common and simple, many assays are far more complex in that they require specific fluids, often of differing types and quantities, to be mixed with a known sample size and distributed in controlled volumes in order to provide quantitative test results, rather than simply qualitative results. These fluids may be, but are not limited to, a buffer solution for dilution, fluids containing antibodies and antigens, microspheres coated with binding agents, cell lysing agents, and other fluids required to manipulate the sample being tested. Diagnostic tests that utilize millifluidic and microfluidic volumes of the fluids are intended to provide an incredibly high degree of specificity, sensitivity, and a precise volume and rate of fluid delivery to achieve as accurate a test result as possible. Nearly all microfluidic tests require the introduction of fluids, control of flow, mixing of fluids and other interactive functions throughout the assay sequence to manipulate the sample being tested and to produce an accurate diagnosis.

Typically, consumable diagnostic devices, meaning the diagnostic device is disposable upon being used, require a companion durable hardware device that interfaces with the consumable diagnostic device to execute the test. The durable hardware performs many functions, one of which is to facilitate transfer the fluids into microfluidic or millifluidic channels formed within the consumable diagnostic device. The introduction of the fluids to the reaction chamber requires precision; including flow rate, volume and timing, so as to best attempt to replicate the laborious protocols of a laboratory, where precession pipettes are employed to obtain quantitative results. Obtaining quantitative test results continues to prove challenging in point-of-care diagnostic devices, and expensive, given the need for the durable hardware. Two challenges common to all assays are the need to control sample collection sizes and maintain precise mixing ratios without loss of sample targets being measured.

SUMMARY OF THE INVENTION

In accordance with one aspect of the invention, a single-use, consumable diagnostic cartridge is provided having a valve member including a translatable fluid passage and a separate translatable sample through port with an underlying registered sample receiving chamber with a fixed capillary volume provided by a geometry at the distal end of the sample receiving chamber which disrupts and halts the capillary propagation.

In accordance with another aspect of the invention, upon translated actuation of the valve member, a precise volume of the sample is segmented from the total sample population and the segmented sample remains in fluid communication with a fluidic channel through which a secondary fluid flushes and carries the sample past the disruptive capillary geometry, thus flushing all of the sample from the fixed capillary channel volume to a detection/analysis chamber.

In accordance with another aspect of the invention, the fluidic channel distal to the sample receiving chamber is comprised of a turbulent inducing, meandering geometry thus providing a homogeneous mixing action between the segmented sample and the secondary fluid.

In accordance with another aspect of the invention, the detection/analysis chamber, containing an air vent to allow venting of air therethrough, resides distal to the fluidic channel allowing measurement of the target(s) with respect to the fixed volume.

In accordance with another aspect of the invention, the total volume of fluid from the proximal end of the sample receiving chamber to the end of the detection/analysis chamber is fixed, thus providing a controlled sample to secondary fluid volume.

In accordance with another aspect of the invention, actuation of the slide valve member containing the sample through port isolates the precise sample volume contained within the sample receiving chamber from the outside environment.

In accordance with another aspect of the invention, actuation of the valve member automatically and simultaneously opens a blister containing the secondary fluid.

In accordance with another aspect of the invention, the process of subsequent segmentation and other fluids may proceed so as to multiply the number of controlled volume and/or mixing processes.

In accordance with another aspect of the invention, a disposable diagnostic device is provided. The disposable diagnostic device includes an upper surface having a sample inlet opening; a lower surface, and a central body disposed between the upper and lower surfaces. The central body has an inlet port, a sample receiving chamber, an analysis chamber and a fluid channel extending between the sample receiving chamber and the analysis chamber. The disposable diagnostic device further includes a rupturable fluid dispensing member operably fixed to the central body and containing a fluid therein for selective fluid communication with the sample receiving chamber. Further yet, the disposable diagnostic device includes a valve member disposed between the upper and lower surfaces. The valve member has a sample through port and a fluid passage, wherein the valve member is selectively moveable between an unactuated closed state to an actuated open state. While in the unactuated closed state, the fluid passage is out of fluid communication with the sample receiving chamber and the sample through port is registered with the sample inlet opening of the upper surface and with the sample receiving chamber of the central body to allow a sample to be disposed into the sample receiving chamber. While in the actuated open state, the fluid passage is moved into fluid communication with the sample receiving chamber to bring the fluid within the fluid dispensing member, upon being ruptured, into fluid communication with the sample disposed in the sample receiving chamber, wherein the fluid readily flows through the inlet port, through the fluid passage to the sample receiving chamber to transport the sample throughout the fluid channel to the analysis chamber.

In accordance with another aspect of the invention, the disposable diagnostic device valve member can be configured to be linearly translatable between the unactuated closed state and the actuated open state.

In accordance with another aspect of the invention, a piercing member can be disposed in the fluid passage, with the piercing member being configured to pierce the rupturable fluid dispensing member automatically upon the valve member being selectively moved from the unactuated closed state to the actuated open state.

In accordance with another aspect of the invention, the piercing member can be biased to automatically extend through the inlet port to pierce the rupturable fluid dispensing member upon the valve member being selectively moved from the unactuated closed state to the actuated open state.

In accordance with another aspect of the invention, the sample receiving chamber can be provided having a port exit with a conically tapered surface everted radially outwardly from the port exit to facilitate the formation of a controlled volume meniscus of the fluid sample.

In accordance with another aspect of the invention, a hydroscopic, gas permeable vent can be provided in the analysis chamber to allow gas to be automatically vented therefrom while performing the test.

In accordance with another aspect of the invention, the rupturable fluid dispensing member can be provided being free of any predefined rupturable or frangible openings.

In accordance with another aspect of the invention, the fluid channel can be provided being serpentine to facilitate mixing the fluid with the sample.

In accordance with another aspect of the invention, a method of performing a diagnostic test on a fluid sample via a disposable diagnostic cartridge is provided. The method includes disposing a sample through an inlet opening in a cover of the disposable diagnostic cartridge, through a sample through port of a translatable valve member of the disposable diagnostic cartridge, and into a sample receiving chamber of the disposable diagnostic cartridge. Then, translating the valve member from an unactuated closed state to an actuated open state to isolate a precise volume of the sample in the sample receiving chamber. Further, rupturing a blister of the disposable diagnostic cartridge and causing fluid to flow from the blister to carry the sample through a fluidic channel in the disposable diagnostic cartridge to an analysis chamber of the disposable diagnostic cartridge. Then, analyzing the sample while in the analysis chamber of the disposable diagnostic cartridge.

In accordance with another aspect of the invention, the method can further include causing a piercing member contained within a portion of the valve member to automatically rupture the blister while translating the valve member.

In accordance with another aspect of the invention, the method can further include automatically forming a controlled volume meniscus of the sample at an exit of the sample receiving chamber upon disposing the sample in the sample receiving chamber.

In accordance with another aspect of the invention, the method can further include forming the controlled volume meniscus of the sample via a conically tapered surface everted radially outwardly from an exit of the sample receiving chamber.

In accordance with another aspect of the invention, the method can further include translating the valve member linearly from the unactuated closed state to the actuated open state.

In accordance with another aspect of the invention, the method can further include venting gas outwardly from the analysis chamber through a hydroscopic, gas permeable vent.

In accordance with another aspect of the invention, the method can further include rupturing the blister with the blister being free of any predefined rupturable or frangible openings.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 4 is a cross-sectional isometric view of the diagnostic cartridge with a slide valve member in an initial, unactuated closed state and a sample through port thereof registered with a sample inlet opening of a cover of the cartridge and a sample receiving chamber of the cartridge;

FIG. 5 is a view similar to FIG. 4 with the slide valve member in an actuated open state, with a lancet shown in a deployed position rupturing an underlying fluid blister and with the sample inlet opening and sample through port closed;

FIG. 6 is an enlarged cross-sectional isometric view of the encircled area 6 of FIG. 5;

DETAILED DESCRIPTION OF PRESENTLY PREFERRED EMBODIMENTS

Figure 1:
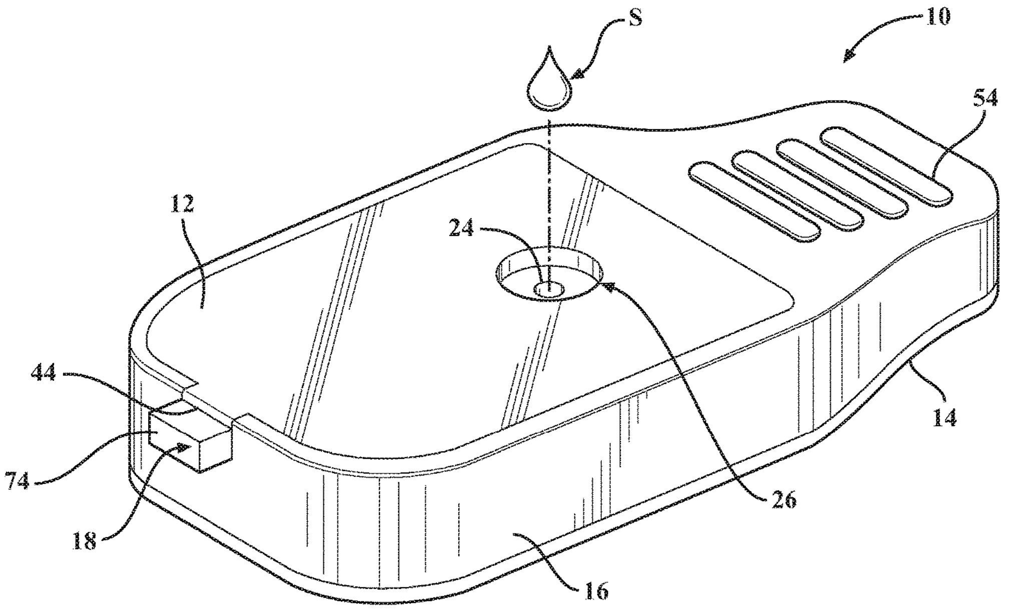
FIG. 1 is an isometric view of a diagnostic cartridge constructed in accordance with one aspect of the invention.
Figure 2:
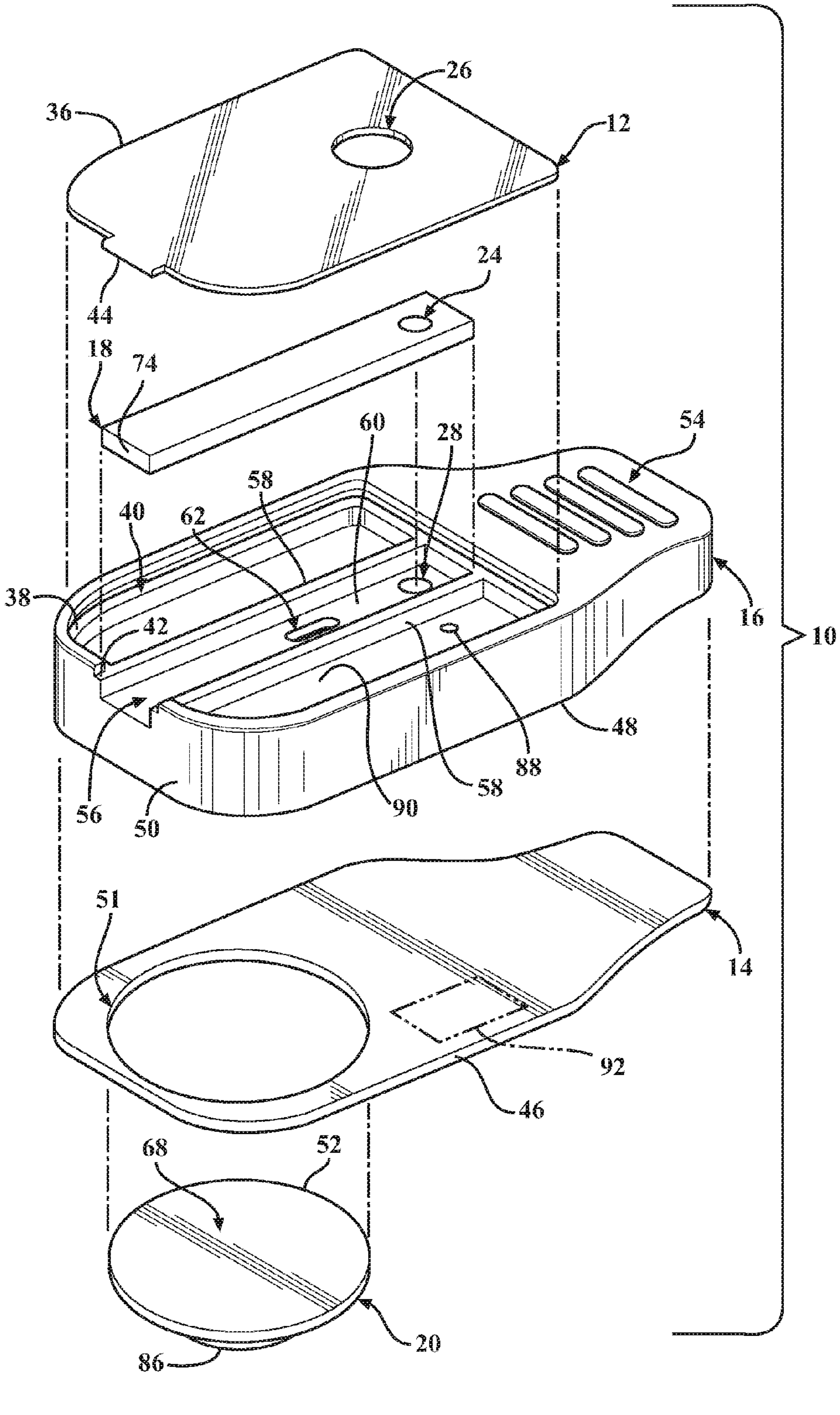
FIG. 2 is an exploded top view of the diagnostic cartridge of FIG. 1.
Figure 3:
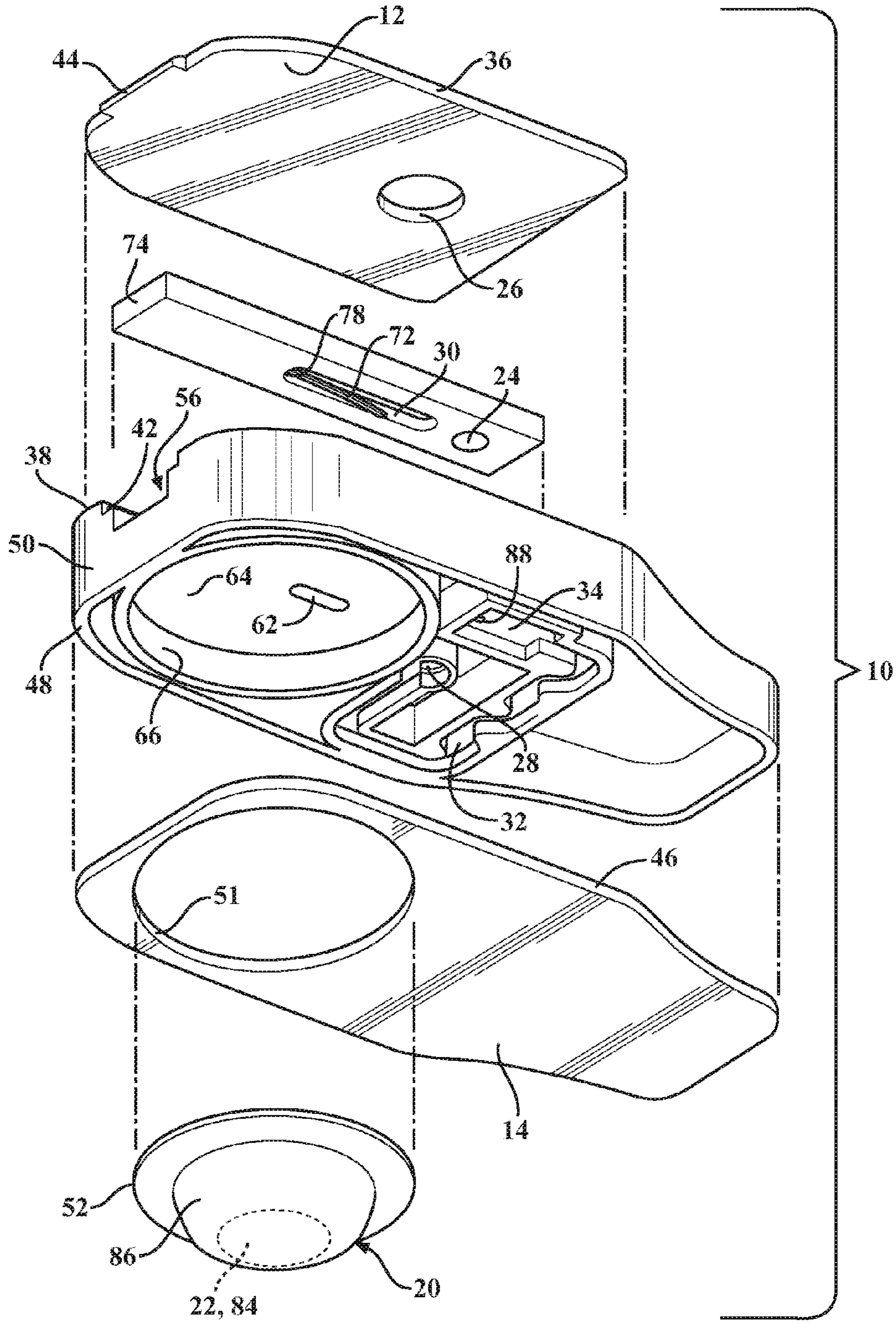
FIG. 3 is an exploded bottom view of the diagnostic cartridge of FIG. 1.
Figure 7:
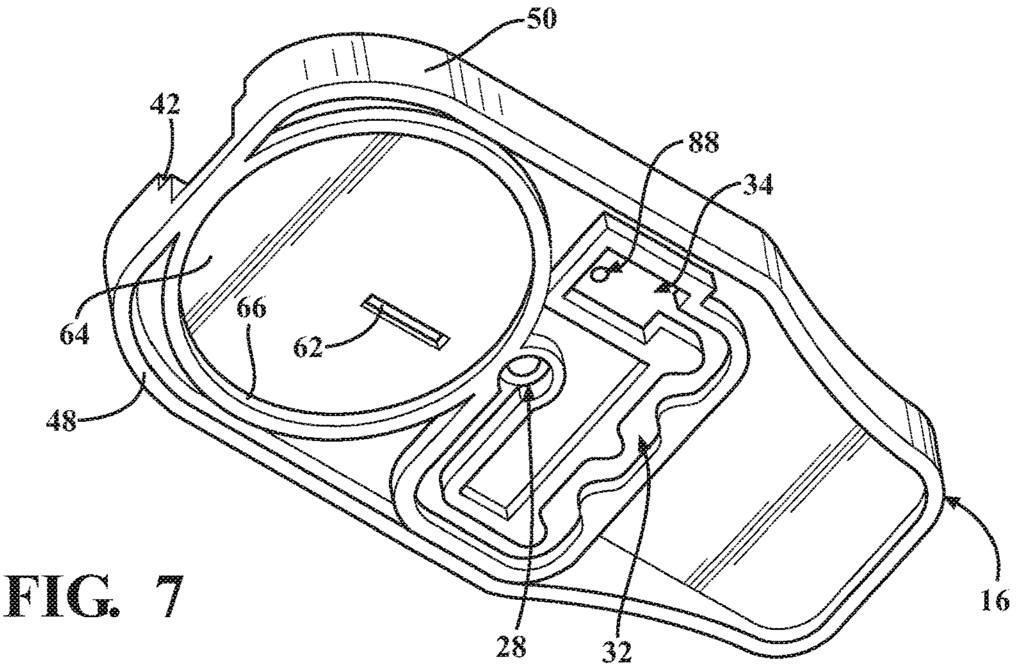
FIG. 7 is an isometric bottom view of a cartridge body of the cartridge of FIG. 1.
Figure 8:
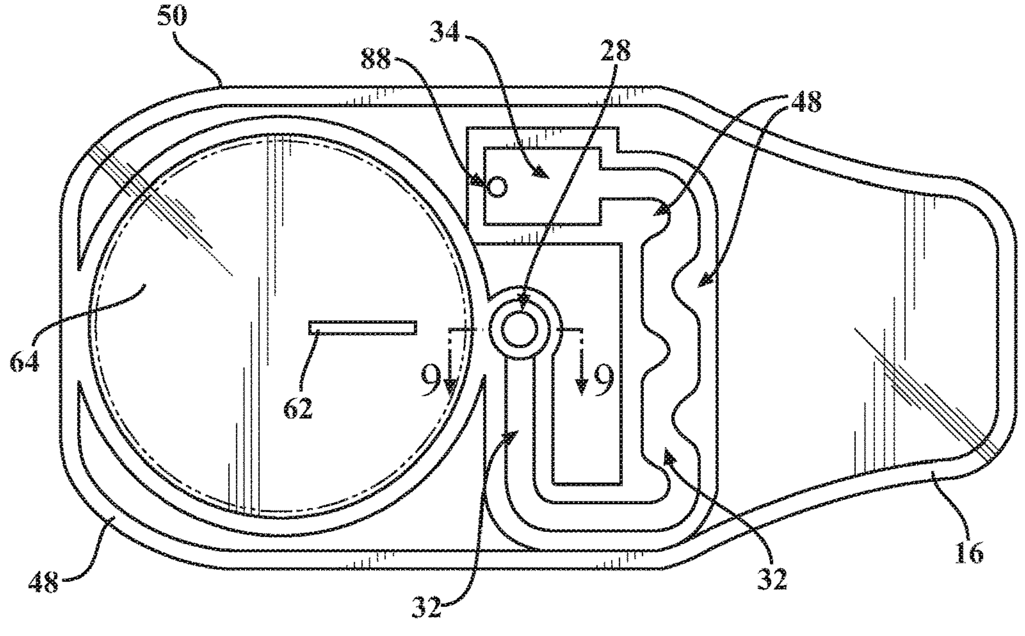
FIG. 8 is an assembled bottom plan view of the diagnostic cartridge of FIG. 1.
Figure 9:
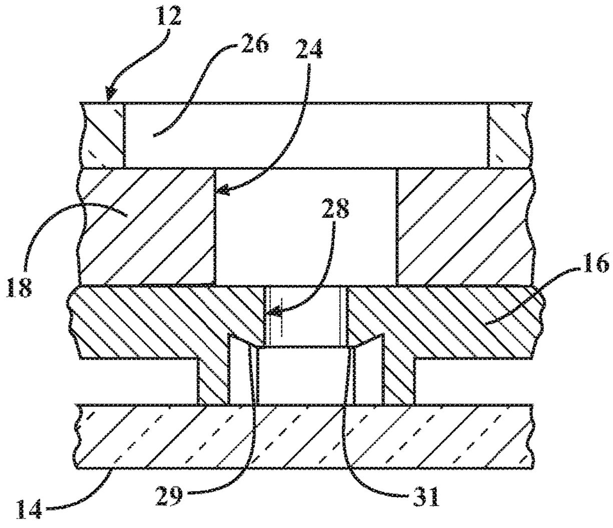
FIG. 9 is an enlarged cross-sectional view taken generally along the line 9-9 of FIG. 8 without a liquid sample present.
Figure 10:
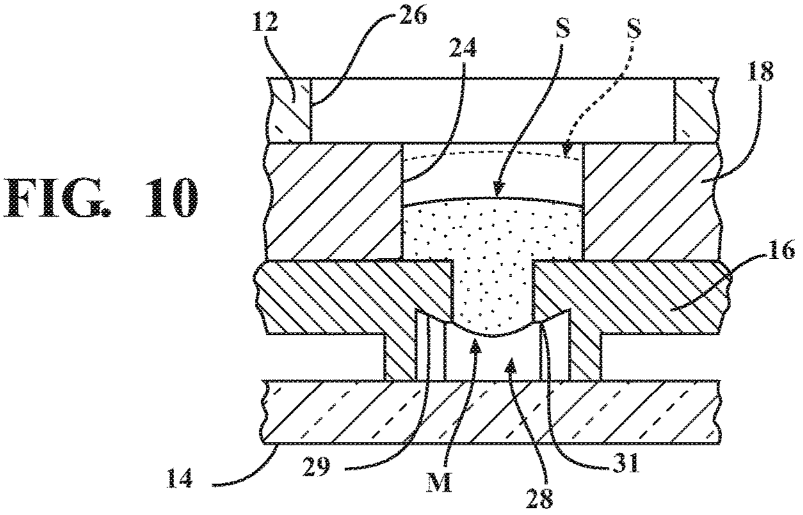
FIG. 10 is a view similar to FIG. 9 with a liquid sample present with the diagnostic cartridge shown in a unactuated state.

Referring in more detail to the drawings, FIG. 1 illustrates a disposable diagnostic cartridge, referred to hereafter as cartridge 10, constructed in accordance with one aspect of the invention for performing qualitative and quantitative analysis on a controlled volume specimen. As best shown in FIGS. 2 and 3, the cartridge 10 has a top or upper surface or layer, also referred to as cover 12, a bottom or lower surface or layer, also referred to as base 14, a central or main body 16 and translatable valve member 18 disposed between the cover 12 and the base 14, and a fluid dispensing member, such as a flexible, compliant blister 20 containing a desired fluid 22 therein. The valve member 18 is operable to be actuated to move between an initial, unactuated closed state (FIG. 4) to an actuated open state (FIG. 5). While in the closed state, the valve member 18 has a sample through port 24 registered with both a sample inlet opening 26 of the cover 12 and with a controlled volume, sample receiving chamber 28 of the cartridge main body 16. As such, a sample S is able to be readily disposed into the sample receiving chamber 28 while the valve member 18 is in the closed state, wherein, as best shown in FIGS. 9 and 10, the controlled volume sample receiving chamber 28 has an integral capillary flow break edge 29 produced by a conically shaped, tapered surface geometry extending in everted diverging relation radially outwardly from a sample port exit 31, such that the sample port exit 31 terminates at a sharp annular edge spaced from and raised above the base 12. The annular sharp edge of the everted capillary flow break edge 29 facilitates the formation of a controlled volume meniscus M of the fluid sample S (FIG. 10). As such, in combination with actuation of the valve member 18, the cylindrical volume of the sample receiving chamber 28 and the controlled volume formation of the meniscus M facilitate providing the desired precise volumetric control (forming a precise volume of the sample S) of the sample S and mixture thereof with a reagent for the test, which in turn provides for consistent, accurate and reliable test results. While in the open state, the valve member 18 has a fluid passage 30 that brings the fluid 22 within the blister 20, upon being ruptured, into fluid communication with the sample S disposed within the sample receiving chamber 28, thereby readily transporting the sample S via intermixing flow of the sample S with the fluid 22 throughout a fluidic mixing channel, also referred to as fluidic channel or channel 32, shown as being formed within the main body 16, to an analysis/detection chamber, referred to hereafter as analysis chamber or simply chamber 34, also shown as being formed in the main body 16.

The cover 12 can be made of any suitable flexible or rigid material, as desired. The cover 12 has an outer periphery 36 sized for mating, bonded engagement with an upper surface 38 of the main body 16. As shown, the outer periphery 36 is received in a recess, referred to as recessed surface 40 (FIG. 2), of the upper surface 38 such that the cover 12 is flush with an outer periphery of the upper surface 38 of the main body 16. To facilitate orienting the cover 12 relative to the main body 16, the upper surface 38 has a laterally extending open slot 42 sized for close receipt of a tab or tongue 44 of the cover 12. Any suitable adhesive or bonding agent can be used, including welding, for example, to fix the cover 12 to the main body 16.

The base 14 can be made of any suitable flexible or rigid material, as desired. The base 14, by way of example and without limitation, has an outer periphery 46 sized for mating, bonded engagement with a lower surface 48 of the main body 16. As shown, the outer periphery 46 is sized to be flush with an outer periphery 50 of the main body 16. The base 14 has a suitably sized opening 51 to accommodate the blister 20. The opening 51 can be sized for a line-to-line fit with an outer periphery 52 of the blister 20, a slightly loose fit, or for a slight interference, overlapping fit therewith. Accordingly, the opening 51 can have the same diameter has the outer periphery 52 of the blister 20, slightly larger, or slight smaller, such that the outer periphery 52 of the blister 20 is in a clearance or overlapping relation with the base 14, depending on the desired construction. Any suitable adhesive or bonding agent can be used, including various forms of welding, for example, to fix the base 14 to the main body 16.

The main body 16 is constructed of any suitable rigid material, and is preferably formed of a molded material to allow economic construction of the intricate details thereof, though it is contemplated that other forms of manufacture could be used. The main body 16 can be provided with a cartridge grip 54 at an end opposite the slot 42. The grip 54 facilitates holding the cartridge 10 during use. The main body 16 further includes a valve receiver channel 56 extending lengthwise in elongate fashion therealong from the slot 42 toward the cartridge grip 54. The valve receiver channel 56 is shown as being straight and being bounded by opposite sidewalls 58 (FIG. 2) that depend (extend downwardly) from the recessed surface 40 of the main body upper surface 38 to a floor 60. A valve inlet port 62 extends through the floor 60 between the sidewalls 58 in a predetermined location above and at least partially aligned with the blister 20 such that the valve inlet port 62 extends through an underlying mount surface 64 on which the blister 20 is mounted. The valve inlet port 62 is shown, by way of example and without limitation, as being off-center relative to a center of the blister 20, and is further shown as being adjacent the outer periphery 52 of the blister proximate the sample through port 24.

The valve member fluid passage 30 is formed as a recessed slot or groove extending into the body of the valve member 18, and is formed being generally elongate, such that it registers in fluid communication with the valve inlet port 62 while the valve member 18 is in both the closed and open states, as discussed further below. The fluid passage 30 includes an extended section, also referred to as lancet pocket 70, that extends from a fluid flow section of the fluid passage 30 toward an actuator end 74 of the valve member 18. The lancet pocket 70 is sized for a close, slight clearance fit of a cutting or piercing member, also referred to as lancet 72, therein. The lancet 72 is constructed having a cutting or piercing edge or end 76 to be moved into a cutting, tearing or piercing relation with a bottom surface 68 of the blister 20 upon moving the valve member 18 from the closed state to the open state. Accordingly, movement of the valve member 18 in sliding relation within the valve receiver channel 56 causes automatic, conjoint movement of the lancet 72 via engagement of a surface, shown best in FIG. 6 as an end wall, also referred to as shoulder 78, of the fluid passage 30 with a drive end 80 of the lancet 72. In one preferred embodiment, the lancet 72 is formed of a heat-settable plastic or heat-shapeable metal material and configured to slide along the floor 60 of the valve receiver channel 56 conjointly with the valve member 18. Actuated movement of the valve member 18 causes the lancet 72 to move from a non-cutting, non-piercing straightened configuration/position (FIG. 4) to a cutting, piercing arcuate configuration/position (FIGS. 5 and 6). The different positions of the lancet 72 are made possible via the lancet 72 having a biased, generally straight shape when in the non-cutting, non-piercing configuration/position as a result of being forcibly flattened or straightened via bias imparted by the floor 60 of the valve receiver channel 56, and an unbiased or relaxed arcuate heat-set or heat-shaped configuration when in the cutting, piercing configuration/position as a result of the bias imparted by the floor 60 being released due to the piercing end 76 being moved out of engagement from the floor 60 and being disposed over and through the valve inlet port 62. Accordingly, the lancet 72 moves automatically from the non-cutting, non-piercing configuration/position to the cutting, piercing configuration/position upon actuation of the valve member 18 to the actuated, open position.

The mount surface 64 is shown as being circular and recessed upwardly from the lower surface 48 of the main body 16. Accordingly, a generally cylindrical cavity is formed and bounded by an annular sidewall 66. The annular sidewall 66 is sized to receive the outer periphery 52 of the blister 20 in a line-to-line or slight clearance fit, wherein a base, also referred to as blister breach surface or bottom surface 68, of the blister 20 is configured to be fixed, such as via any suitable bonding or attachment mechanism, to the mount surface 64 of the main body 16.

The blister 20 is formed of any suitable flexible material or materials to bound and encapsulate a dispensing reservoir 84 of a predetermined volume. The dispensing reservoir 84 contains a predetermined volume of a sealed fluid reagent, referred to hereafter as fluid 22, therein, or it could be air, depending on the nature of the test to be performed. The fluid 22 contained in dispensing reservoir 84 can be of any desired type of fluid, again depending on the nature of the test to be performed, including an inactive, non-reactive fluid, such as water, for example, or an active, reactive fluid, such as a reagent capable of lysing a cell. The blister 20, as shown by way of example and without limitation, includes the bottom layer or surface 68, formed without any predefined rupturable or frangible valve, opening or otherwise, and an upper layer 86. Though the bottom surface 68 is described as being valve or opening free, it is contemplated that a predefined valve or opening could be formed in the bottom surface 68, if desired, though not necessary as a result of the novel lancet 72. The upper layer 86 can be formed of the same type of material as the lower layer 68, or from a different type of material, as desired. The upper layer 86 is sufficiently sized to allow the fluid 22 disposed therein to create a bulbous, expanded portion bounding the reservoir 84, wherein the upper layer 86 is flexible and tough, thereby allowing the bulbous portion to be depressed and actuated upon moving the valve member 18 to the open position. The lower and upper layers 68, 86 can be bonded to one another about their respective out peripheries via any suitable bonding process upon disposing the fluid 22 therebetween, such as a suitable welding to adhering process.

In use, the cartridge 10 is first provided with the valve member 18 in the closed position (FIGS. 1 and 4). The cartridge 10 remains in this pre-use state until a test is desired to be performed. When a test is to be performed, a fluid sample S, such as a droplet of blood, by way example and without limitation, is deposited through the sample inlet opening 26, through the sample through port 24 and into the sample receiving chamber 28, which are all aligned in generally concentric relation with one another (FIG. 9). During initial deposit of the sample S, the sample S fills the sample receiving chamber 28, forming the precise volume meniscus M, as discussed above, wherein the total sample volume occupying the sample receiving chamber and including the meniscus M is provided having a predetermined volume, such as about 10 μl, for example, and wherein a portion of the sample S can also fill or substantially fill the sample through port 24 as well (FIG. 10).

Figure 10A:
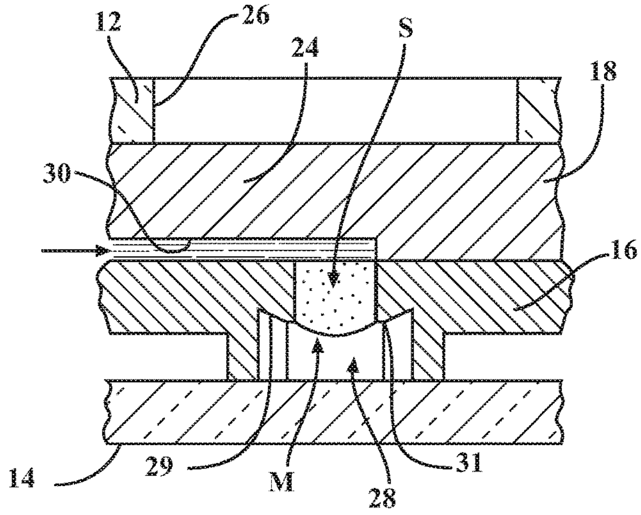
FIG. 10A is a view similar to FIG. 10 with the diagnostic cartridge shown in an actuated state.

Upon depositing the sample S in the sample receiving chamber 28, the valve member 18 is actuated by pushing the actuator end 74 of the valve member 18 toward the main body 16, whereupon the valve member 18, configured for close, snug sliding receipt in the valve receiver channel 56, slides along the valve receiver channel 56 until the actuator end 74 is flush or substantially flush with the main body 16 (FIG. 5). Upon actuating the valve member 18, the fluid passage 30 is moved to bridge a fluid barrier formed by the floor 60 of the main body 16, while in the pre-use state, thereby bringing the valve inlet port 62 into fluid communication with the sample receiving chamber 28, while also remaining in fluid communication with the valve inlet port 62. Accordingly, the valve inlet port 62 and the sample receiving chamber 28 are now brought into potential fluid communication with one another. Further, as shown in FIG. 10A, the portion of the sample S that is contained in the sample through port 24 is shifted laterally out of fluid communication from the precise volume sample portion S, such as about 10 for example, contained in the sample receiving chamber 28. Accordingly, only the precise and desire volume of the sample S within the sample receiving chamber 28 is in potential fluid communication with the valve inlet port 62. Further and simultaneous with the sliding movement of the valve member 18 within the valve receiver channel 56, the lancet 72 is caused to slide along the floor 60 of the main body 16 as a result of the drive end 78 of the lancet 72 being pushed by the shoulder 78, whereupon the piercing end 76 clears free from the floor 60 and enters the valve inlet port 62. As the piercing end 76 enters the valve inlet port 62, the bias imparted by by the floor 60 tending to straighten the lancet 72 is released, and as such, the piercing end 76 relaxes and automatically curls downwardly through the valve inlet port 62 and into piercing, cutting and/or tearing engagement with the bottom surface 68 of the blister 20. As such, an opening is formed in the bottom surface 68 (FIG. 6), and the fluid 22 is free to be expelled from the blister 20.

Upon selectively piercing the bottom surface 68 and forming an opening therein, the upper layer 86 of the blister 20 can be readily depressed and substantially flattened, whereupon the fluid 22 initially contained within the blister 20 is freely dispensed therefrom through the valve inlet port 62, through the fluid passage 30 extending over the floor 60 of the main body 16 and into and through the sample receiving chamber 28. Thus, the fluid 22 and sample S flow downstream from the sample receiving chamber 28 through the fluidic channel 32. Accordingly, as the fluid 22 carries the precise volume of the sample S from the sample receiving chamber 28 through the fluidic channel 32, which is shown as being meandering and serpentine, the fluid 22 and sample S are mixed, as a result of the turbulence facilitated by the meandering, serpentine flow path, to form a homogenous mixture of the sample S and the fluid 22, wherein the homogenous mixture flows into the analysis/detection chamber 34. To facilitate flow of the mixture into the chamber 34, excess gas can be vented through a gas vent provided via a fluid impervious, hydrophobic membrane 88, also referred to as air vent 88. The air vent 88 is shown as being disposed in a wall of the sample detection chamber 34, with the vent 88 allowing gas to flow into a vent chamber 90 (FIG. 2). Upon being received in the chamber 34, the sample S can be analyzed for a variety of factors, such as number of neutrophil cells, or otherwise. The analysis can be performed through the base 14, if provided as a clear member, otherwise, a clear region, such a clear window 92, can be provided in the base 14 to allow an analysis to be performed on the homogenous sample mixture within the detection chamber 34.

The foregoing description of the embodiments has been provided for purposes of illustration and description. It is not intended to be exhaustive or to limit the disclosure or claims. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure and claims, wherein the claims ultimately define the scope of the invention.

What is claimed is:

1. A disposable diagnostic device, comprising:

an upper surface having a sample inlet opening;

a lower surface;

a central body disposed between said upper and lower surfaces, said central body having an inlet port, a sample receiving chamber, an analysis chamber downstream from said sample receiving chamber and a fluid channel extending between said sample receiving chamber and said analysis chamber;

a rupturable fluid dispensing member operably fixed to said central body upstream from said sample receiving chamber and containing a fluid therein for selective fluid communication with said sample receiving chamber; and a valve member disposed between said upper and lower surfaces, said valve member having a sample through port and a fluid passage, said valve member being selectively moveable between an unactuated closed state to an actuated open state, while in said unactuated closed state, said fluid passage being out of fluid communication with said sample receiving chamber, thereby interrupting a fluid flow path between said fluid dispensing member said sample receiving chamber, and said sample through port being registered with said sample inlet opening of said upper surface and with said sample receiving chamber of said central body to allow a sample to be disposed into said sample receiving chamber, and while in said actuated open state, said fluid passage being moved into fluid communication with said sample receiving chamber to bring said fluid within said fluid dispensing member, upon being ruptured, into fluid communication with the sample disposed in said sample receiving chamber, wherein said fluid readily flows through said inlet port, through said fluid passage to said sample receiving chamber to transport the sample throughout said fluid channel to said analysis chamber.

2. The disposable diagnostic device of claim 1, wherein said valve member is linearly translatable between said unactuated closed state and said actuated open state.

3. The disposable diagnostic device of claim 1, further including a piercing member disposed in said fluid passage, said piercing member being configured to pierce said rupturable fluid dispensing member automatically upon said valve member being selectively moved from the unactuated closed state to the actuated open state.

4. The disposable diagnostic device of claim 3, wherein said piercing member is biased to automatically extend through said inlet port to pierce said rupturable fluid dispensing member upon said valve member being selectively moved from the unactuated closed state to the actuated open state.

5. The disposable diagnostic device of claim 1, wherein said sample receiving chamber has a port exit with a conically tapered surface everted radially outwardly from said port exit to facilitate the formation of a controlled volume meniscus of the fluid sample.

6. The disposable diagnostic device of claim 1, further including a hydroscopic, gas permeable vent in said analysis chamber.

7. The disposable diagnostic device of claim 1, wherein said rupturable fluid dispensing member is free of any predefined rupturable or frangible opening.

8. The disposable diagnostic device of claim 7, wherein said rupturable fluid dispensing member is compliant.

9. The disposable diagnostic device of claim 1, wherein said fluid channel is serpentine to facilitate mixing the fluid with the sample.

10. The disposable diagnostic device of claim 1, wherein said upper surface is formed by a cover, said lower surface is formed by a base, said cover and said base being fixed to said central body.

11. The disposable diagnostic device of claim 1, wherein said base has a clear region positioned over said analysis chamber to allow the sample to be analyzed.

* * * * *